United States Patent
Dawson

(10) Patent No.: US 7,842,072 B2
(45) Date of Patent: Nov. 30, 2010

(54) SPINAL FIXATION DEVICE WITH VARIABLE STIFFNESS

(75) Inventor: John Dawson, Chaska, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 350 days.

(21) Appl. No.: 11/377,476

(22) Filed: Mar. 16, 2006

(65) Prior Publication Data

US 2007/0233075 A1    Oct. 4, 2007

(51) Int. Cl.
*A61B 17/70* (2006.01)
(52) U.S. Cl. ............... 606/263; 606/257; 606/279
(58) Field of Classification Search ........... 606/61, 606/246, 254–259, 263; 385/62, 81
See application file for complete search history.

(56) References Cited

U.S. PATENT DOCUMENTS

| | | | |
|---|---|---|---|
| 5,042,982 A * | 8/1991 | Harms et al. ............ | 606/61 |
| 5,395,374 A * | 3/1995 | Miller et al. ............ | 606/74 |
| 5,782,831 A | 7/1998 | Sherman et al. | |
| 6,290,700 B1 * | 9/2001 | Schmotzer ............ | 606/61 |
| 7,011,658 B2 * | 3/2006 | Young ............ | 606/61 |
| 2002/0032450 A1 * | 3/2002 | Trudeau et al. ............ | 606/103 |
| 2002/0198532 A1 | 12/2002 | Michelson | |
| 2004/0049190 A1 * | 3/2004 | Biedermann et al. ............ | 606/61 |
| 2005/0261695 A1 | 11/2005 | Cragg et al. | |
| 2006/0111715 A1 | 5/2006 | Jackson | |
| 2006/0195090 A1 * | 8/2006 | Suddaby ............ | 606/61 |
| 2007/0016200 A1 | 1/2007 | Jackson | |
| 2007/0055244 A1 | 3/2007 | Jackson | |
| 2007/0233085 A1 * | 10/2007 | Biedermann et al. ............ | 606/61 |
| 2007/0233089 A1 * | 10/2007 | DiPoto et al. ............ | 606/61 |

(Continued)

FOREIGN PATENT DOCUMENTS

DE      10348329 B3 *    2/2005

(Continued)

OTHER PUBLICATIONS

G. Dubois, B. de Germany, Nicolas S. Schaerer and P. Fennema; Dynamic Neutralization: A New Concept for Restabilization of the Spine, Lippincott Williams & Wilkins Healthcare, Publication pp. 233-240, 1999.

(Continued)

*Primary Examiner*—Thomas C Barrett
*Assistant Examiner*—Andrew Yang
(74) *Attorney, Agent, or Firm*—Crompton, Seager & Tufte, LLC

(57) ABSTRACT

A device for spinal stabilization includes bone anchors, a metal cord, and a spacer. The materials of the cord and spacer are chosen to allow the physician to customize the stiffness of the stabilization device based on a particular patient's needs. Each bone anchor has a clamping mechanism for securing the cord to the bone anchor. In an assembled and implanted state of the device, the spacer is positioned between two neighboring bone anchors, thereby impeding the motion of the bone anchors toward each other; the cord is clamped to the bone anchors, thereby impeding the motion of the bone anchors away from each other. By increasing or decreasing the tension in the cord during implantation, the physician can create a stabilization device that is either relatively stiff or relatively flexible to accommodate the specific needs of the patient.

21 Claims, 7 Drawing Sheets

| U.S. PATENT DOCUMENTS | | |
|---|---|---|
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |

FOREIGN PATENT DOCUMENTS

| EP | 0669109 | * | 8/1995 |
|---|---|---|---|
| EP | 0669109 A1 | | 8/1995 |

OTHER PUBLICATIONS

W. Schmoelz, J. F. Huber, T. Nydegger, L. Claes and H. J. Wilke; Dynamic Stabilization of the Lumbar Spine and Its Effects on Adjacent Segments, Journal of Spinal Disorders & Techniques, Vo. 16, No. 4, Publication pp. 418-423, 2003.

* cited by examiner

SPINAL FIXATION DEVICE WITH VARIABLE STIFFNESS

FIELD

The invention relates to spinal fixation systems and devices. More particularly, the invention relates to an improved fixation device having bone anchors and interconnecting components.

BACKGROUND

Traditional spinal stabilization systems include the type which has multiple bone anchors for attaching to the respective vertebrae, and a linking member secured to the bone anchors to prevent or limit the motion between the vertebrae. Anchors typically include pedicle screws and/or hooks. Linking members typically include rods and/or plates. Alternatively, the linking member may be a substantially flexible cord, which permits relative motion between the stabilized vertebrae, and a resilient spacer between each pair of linked bone anchors. One exemplary system is made of braided Polyethylene Terephthalate (PET; available under the Sulene™ brand from Sulzer Orthopedics, Ltd., Baar, Switzerland). An exemplary spacer is made of Polycarbonate Urethane (PCU, also available under the Sulene™ brand name from Sulzer Orthopedics, Ltd.).

In the prior exemplary systems, the spacer generally operates to resist, without completely preventing, motion of the bone anchors toward each other, while the cord operates to resist motion of the bone anchors away from each other. Because the spacer and cord are generally more flexible than rigid metal rods or plates, systems employing a cord and/or spacer arrangement generally permit movement between vertebrae and thus provide a more dynamic stabilization system than those employing rigid linking members. Additionally, the interconnections between the anchors, spacers, and cords may permit relative motions that are meant to be prevented with rigid metal systems, which also provide a more dynamic stabilization system than those employing rigid linking members.

Each of the foregoing types of systems may have advantages and disadvantages in a given patient condition. Because of the diverse patient conditions requiring treatment, however, there is a need in the art for a spinal stabilization system that combines the advantages of rigid and dynamic stabilization systems, and permits the physician to modify the rigidity of the system based on the needs of the patient.

SUMMARY

The invention disclosed herein is aimed at providing a method and apparatus for providing improved spinal treatment to individual patients. According to one embodiment, the present invention is an implantable orthopedic stabilization device comprising a cord, at least one pair of bone anchors, wherein each bone anchor includes a bone attachment portion adapted to engage a vertebra, and a head portion attached to the bone attachment portion and including a cord receiving portion and a clamping mechanism adapted to secure the cord to the bone anchor, and a substantially incompressible spacer having a channel sized to receive the cord therethrough. The spacer is adapted to be positioned between and maintain a predetermined spacing between the head portions of the at least one pair of bone anchors. The spacer further includes an end surface configured such that the end surface can articulate along a face of at least one of the head portions of the at least one pair of bone anchors.

In another embodiment, the present invention is a method of stabilizing a portion of a spinal column of a patient comprising implanting first and second bone anchors into respective vertebrae with a substantially incompressible spacer positioned between head portions of the bone anchors, wherein each head portion has a cord receiving portion, and wherein the spacer comprises a channel adapted to receive a cord therethrough. Next, the method includes passing a cord through the cord receiving portions and the channel, and then securing the cord to at least one of the bone anchors. Next, the method includes applying a tensile load to the cord such that the head portions exert a compressive force on the spacer with a face of each of the head portions bearing upon one of a first and second end surface of the spacer. The step of applying the tensile load further includes setting the tensile load such that the compressive force permits a desired amount of articulation of the faces of the head portions along the respective end surfaces of the spacer.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

BRIEF DESCRIPTION OF THE DRAWINGS

The objects and advantages of the invention will become apparent upon reading the following detailed description and upon reference to the drawings in which.

Figure 1:
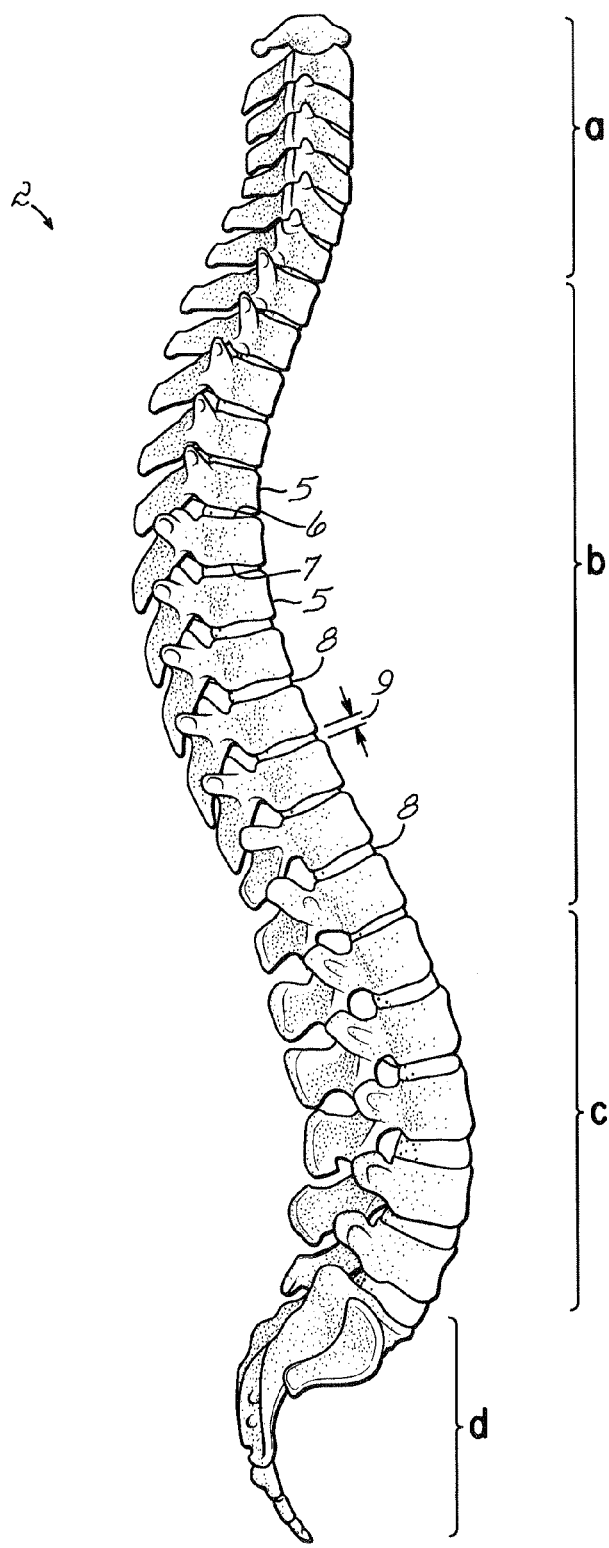
FIG. 1 is a lateral elevation view of a human spinal column.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

FIG. 1 illustrates a human spinal column 2 including vertebrae 5 belonging to one of a cervical region a, a thoracic region b, a lumbar region c and a sacral region d of the spinal column 2. Each vertebra 5 includes a superior end plate 6 and an inferior end plate 7. An intervertebral disc is positioned in an intervertebral space 9 between adjacent vertebrae 5.

Figure 2:
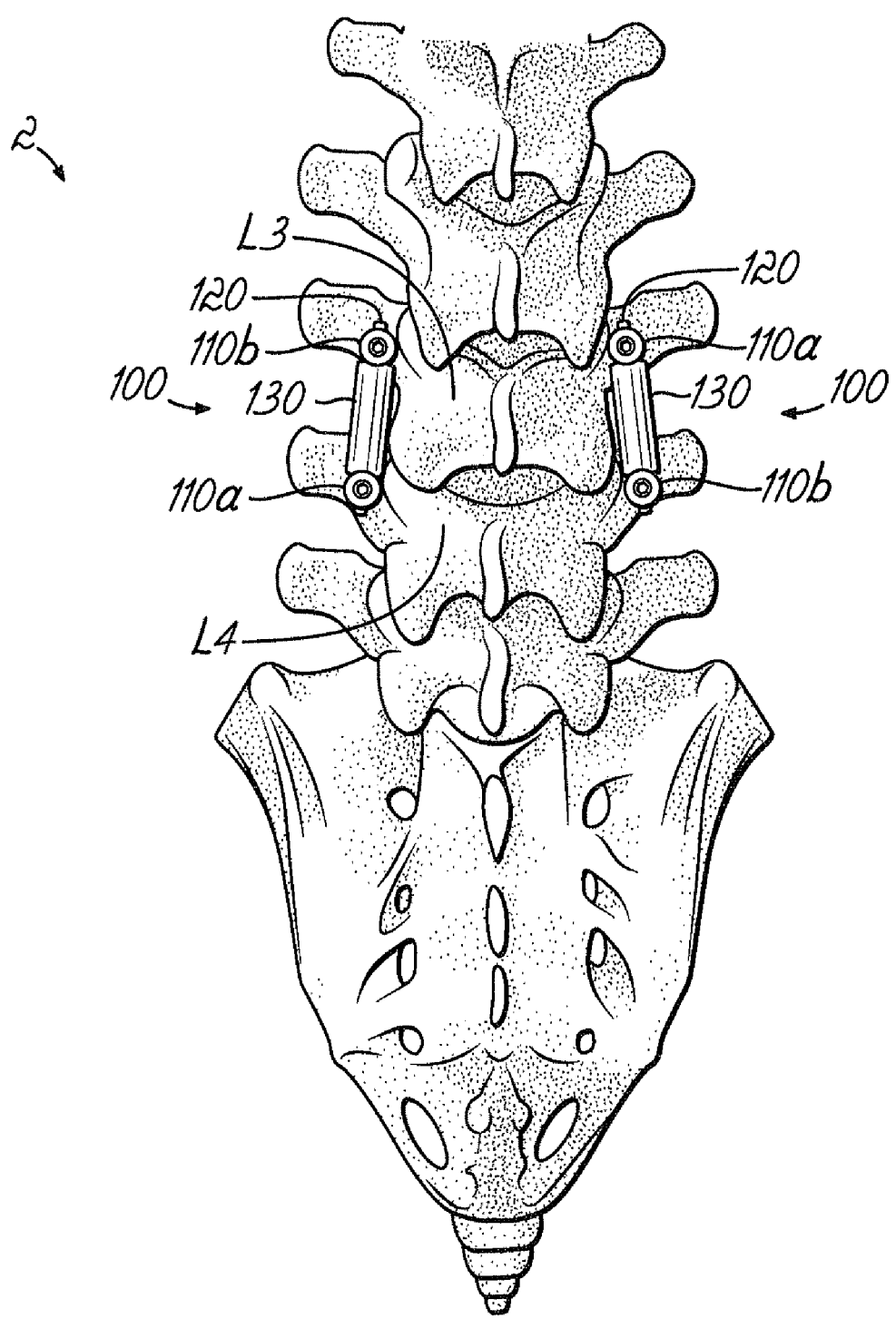
FIG. 2 schematically illustrates a posterior elevation view of the human spinal column with two spinal stabilization devices, according to one embodiment of the present invention, implanted therein.

FIG. 2 is a posterior elevation view of a patient's spinal column 2 into which a pair of spinal stabilization devices 100 according to the present invention are implanted between vertebrae L3 and L4. As shown in FIG. 2, each of the stabilization devices 100 includes a pair of bone anchors, which in this case are pedicle screws 110a and 110b, a cord 120, and a spacer 130 which, as discussed in more detail below, is substantially non-compressible and substantially rigid. As illustrated, each pedicle screw 110a, 110b is driven into a respective vertebra 5. In the illustrated embodiment, the pedicle screw 110a is implanted in the L3 vertebra, and the pedicle screw 110b is implanted in the L4 vertebra. As will be understood by those skilled in the art, however, fixation of other vertebral pairs can be accomplished using the device of the present invention.

Figure 3:
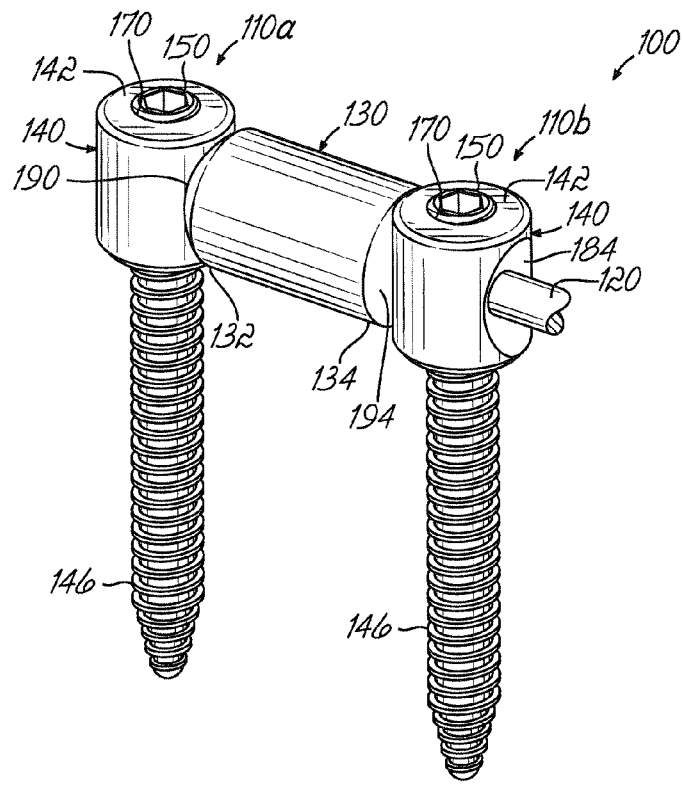
FIG. 3 is a perspective view of the spinal stabilization device depicted in FIG. 2.

FIG. 3 is a perspective view of the stabilization device 100 according to one embodiment of the present invention. As illustrated in FIG. 3, each pedicle screw 110a and 110b includes a head portion 140 with a top surface 142, and a threaded shank portion 146. As will be understood by those skilled in the art, the threaded shank portions 146 are adapted for implantation into a vertebra 5 of the patient. Each head portion 140 includes a threaded set screw 150.

As illustrated, the spacer 130 includes end portions 132 and 134, and is disposed between and in contact with the pedicle screws 110a and 110b. The cord 120 is a cord, cable or wire and is threaded through the spacer 130 and clamped to each pedicle screw 110a and 110b using the set screws 150. In other embodiments, other clamping mechanisms may be used besides set screws 150 to secure the cord 120 in the pedicle screws 110a and 110b. When so clamped, the cord 120 serves to substantially prevent displacement of the screw heads 140 of the pedicle screws 110a and 110b away from each other. The spacer 130 operates to maintain the relative spacing of the pedicle screws 110a, 110b, and to substantially prevent displacement of the screw head 140 of the pedicle screws 110a and 110b toward each other.

In the illustrated embodiment, the cord 120 and the spacer 130 each have a generally cylindrical cross-sectional shape, although in other embodiments, they may have different shapes (e.g., rectangular, elliptical).

Figure 4:
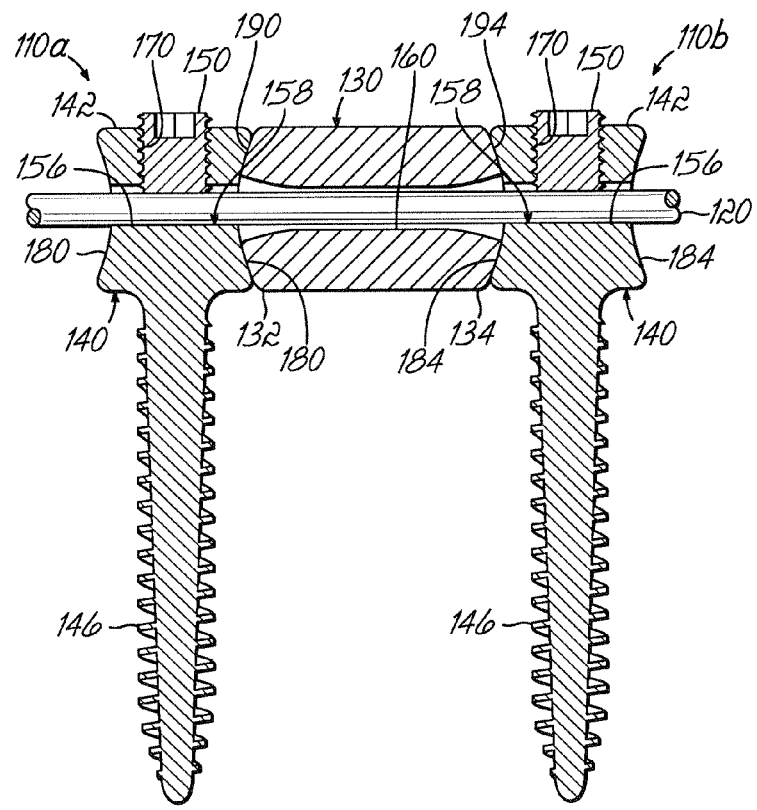
FIG. 4 is a cross-sectional schematic view of the spinal stabilization device depicted in FIG. 3.

FIG. 4 is a cross-sectional view of the spinal stabilization device 100. As shown in FIG. 4, each screw head 140 includes a screw aperture 156 defined by an inner wall 158. As discussed in more detail below, the aperture 156 operates as a cord receiving portion of the screw head 140. A threaded hole 170 extends from the screw aperture 156 to the top surface 142. As further shown, the spacer 130 includes a channel 160 positioned to generally align with the screw apertures 156 in the pedicle screws 110a and 110b such that the cord 120 can be extended through the screw apertures 156 and the channel 160. As illustrated, in each of the pedicle screws 110a, 110b, the threads of the sets screws 150 match the threads of the threaded hole 170 such that each set screw 150 can be turned to advance into the screw apertures 156 to clamp the cord 120 against the inner wall 158.

As further shown, the screw head 140 of each of the pedicle screws 110a and 110b may include generally spherical concave faces 180 and 184 disposed approximately 180 degrees apart. Additionally, each of the end portions 132 and 134 of the spacer 130 may include a generally spherical convex face 190 and 194. As shown, the generally convex faces 190 and 194 are sized and shaped to mate with the generally concave faces 180 and 184, respectively. In some embodiments (not shown), the faces 180, 184 of the screw heads 140 may be generally spherical convex faces, and accordingly, the mating faces 190, 194 of the spacer 130 have concave profiles. Alternatively, one of the faces 180 and 184 may be concave, and the other convex, in which case, the respective matching face 190, 194 of the spacer 130 will be profiled to match as appropriate.

The illustrated configuration operates to optimize the contact stress and friction between the end portions 132, 134 of the spacer 130 and the pedicle screw heads 140. Additionally, this embodiment further permits three-dimensional angular displacement of the pedicle screws 110a and 110b relative to the spacer 130 by allowing the concave faces 180 and 184 to rotatably articulate along the convex faces 190 and 194, respectively, of the spacer 130. As further shown, to permit such angular displacement while minimizing wear to the metal cord 120 and preventing kinking of the cord 120 by the ends of the spacer 130, the channel 160 may flare outward such that the channel 160 is larger near the end portions 132 and 134 than near the middle of the spacer 130.

In yet other embodiments (not shown), the faces 180, 184, 190, and 194 may be generally flat, thus shaped to permit relative rotation of the spacer 130 relative to the screw heads 140 in one dimension defined by the mating flat faces. In one such embodiment the screw faces 180 and 184 may not be perpendicular to the axis of the shank of the screw 146, thereby permitting the device 100 to adapt to a patient's anatomy or pathology.

Figure 5:
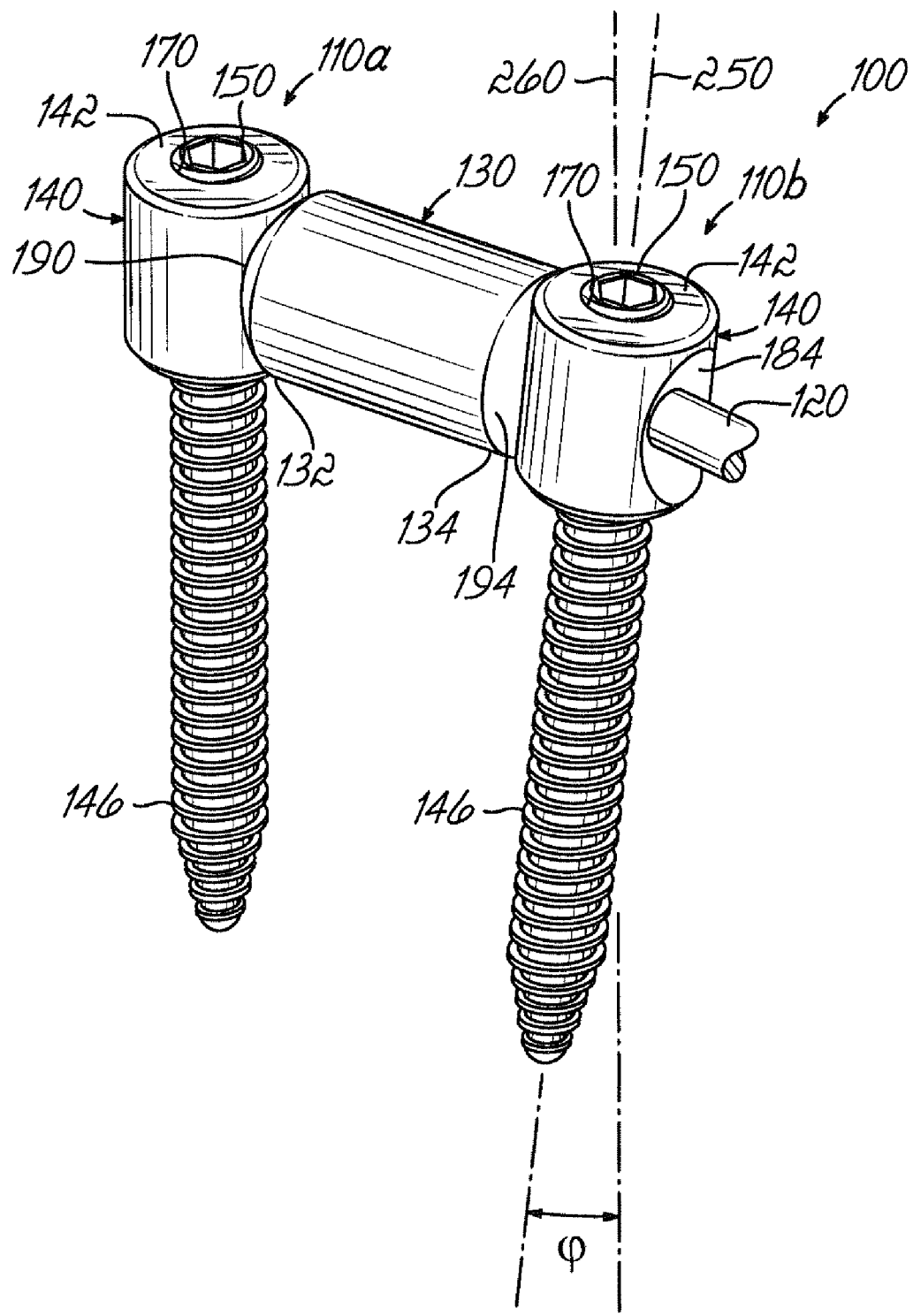
FIG. 5 is a perspective view of the spinal stabilization device shown in FIG. 3, with one of the pedicle screws tilted relative to its position shown in FIG. 3.

FIG. 5 is a perspective view of the stabilization device 100 in which the threaded shank portion 146 of the pedicle screw 110b is tilted toward the pedicle screw 110a. As shown, the longitudinal axis 250 of the pedicle screw 110b is shown to have tilted toward the other pedicle screw 110a by an angle φ from its original position 260 in which the shank portions 146 of the pedicle screws 110a and 110b are substantially parallel. As will be apparent to those skilled in the art, tilting of the pedicle screw 110b as shown in FIG. 5 would not be possible if the interface between the spacer 130 and pedicle screw heads 140 were not the convex/concave configuration according to one aspect of the present invention. Tilting of the screw 110a relative to the screw 110b permits the stabilization device 100, when implanted, to have the proper relative configuration with respect to anatomic features such as the vertebral end plates 6 and 7.

The spacer 130 can be of any suitable material that is substantially rigid and substantially non-compressible. As used in this context, "rigid" means having a stiffness greater than that of the unreconstructed spine, and "non-compressible" means having a compressive strength sufficient to effectively prevent the heads 140 of the pedicle screws 110, 110b from being displaced toward each other under loads created by the patient's bodily movements when the device 100 is implanted as shown in FIG. 2. Suitable materials include metals or alloys, such as titanium and its alloys, stainless steel, ceramic materials, rigid polymers including polyetheretherketone (PEEK™), and substantially rigid and non-compressible composite materials.

The cord 120 is generally configured and sized to be substantially resistant to strain or elongation under tensile loads that may be applied by the patient's bodily movements (e.g., bending and twisting of the spinal column). In one embodiment, the cord 120 may be a biocompatible metal (e.g., titanium and its alloys, stainless steel) wire or cable. Such a cord 120 can be tensioned much more tightly than a polymeric cord, thereby creating a stiffer stabilization system than existing dynamic systems. Thus, by varying tension in the cord 120, the spinal stabilization device 100 can therefore achieve a wider range of flexibility than a device with a polymeric cord.

Thus, in the assembled and implanted state of the device 100, the cord 120 effectively prevents displacement of the heads 140 of the pedicle screws 110a, 110b away from each other. The substantially incompressible spacer 130 substantially prevents movement of the heads 140 of the pedicle screws 110a, 110b toward each other.

In operation, the pedicle screws 110a and 110b are attached to their respective vertebrae, in the embodiment illustrated in FIG. 2, the L3 and L4 vertebrae. The cord 120 is threaded though the screw apertures 156 and the spacer aperture 160, with the spacer 130 sequenced between the pair of pedicle screws 110a, 110b. The cord 120 is then tensioned to a desired amount against the pedicle screws 110a, 110b so that the pedicle screws 110a, 110b are biased against and exert a compressive load on the spacer 130 and the concave faces 180, 184 bear upon the convex faces 190, 194 of the spacer 130. The physician may vary or customize the stiffness of the stabilization device 100 by adjusting the tension applied to the cord 120. In general, the greater the tension in the cord 120, the more frictional resistance will impede articulation of the concave faces 180 and 184 along the convex faces 190 and 194. Thus, the tension in the cord 120 in the assembled and implanted stabilization device 100 generally determines the overall stiffness of the device.

For example, the stabilization device 100 may be made substantially rigid by tensioning the cord 120 to a high degree. In such a case, the large frictional forces produced substantially prevent articulation of the convex faces 180 and 184 along the concave faces 190 and 194 of the spacer 130. Alternatively, the physician may choose to apply a lesser degree of tension to the cord 120, thus allowing articulation of the convex faces 180, 184 along the concave faces 190, 194, which in turn creates a more flexible stabilization device 100. Cord tension may also be varied from left side to right side. In such case, the cord 120 may be tensioned to a high degree between pedicle screws 110a and 110b on one side but tensioned to a lesser amount on the other side. This may be advantageous for patients requiring differing amounts of stabilization between left and right sides due to their disease (e.g., deformity or scoliosis). The amount of tension applied can thus be varied based on the particular patient's needs. In those cases where the tension in the cord 120 is minimal, or just enough to bring the various parts of the stabilization device 100 in contact, there may be very little resistance to articulation. In such cases the stabilization device 100 may predominantly provide the desired spacing between the vertebrae.

Tensioning of the cord 120 can be done, for example, by tightening one of the set screws 150 to clamp the cord 120 to one of the pedicle screws 110a or 110b and then tensioning the cord 120 against the other pedicle screw 110a or 110b. The set screw 150 of the second pedicle screw 110a or 110b is then tightened to clamp the cord 120 to that pedicle screw 110a or 110b. The tension in the cord 120 is thus maintained, and the pedicle screws 110a, 110b remain biased against the spacer 130.

Figure 6:
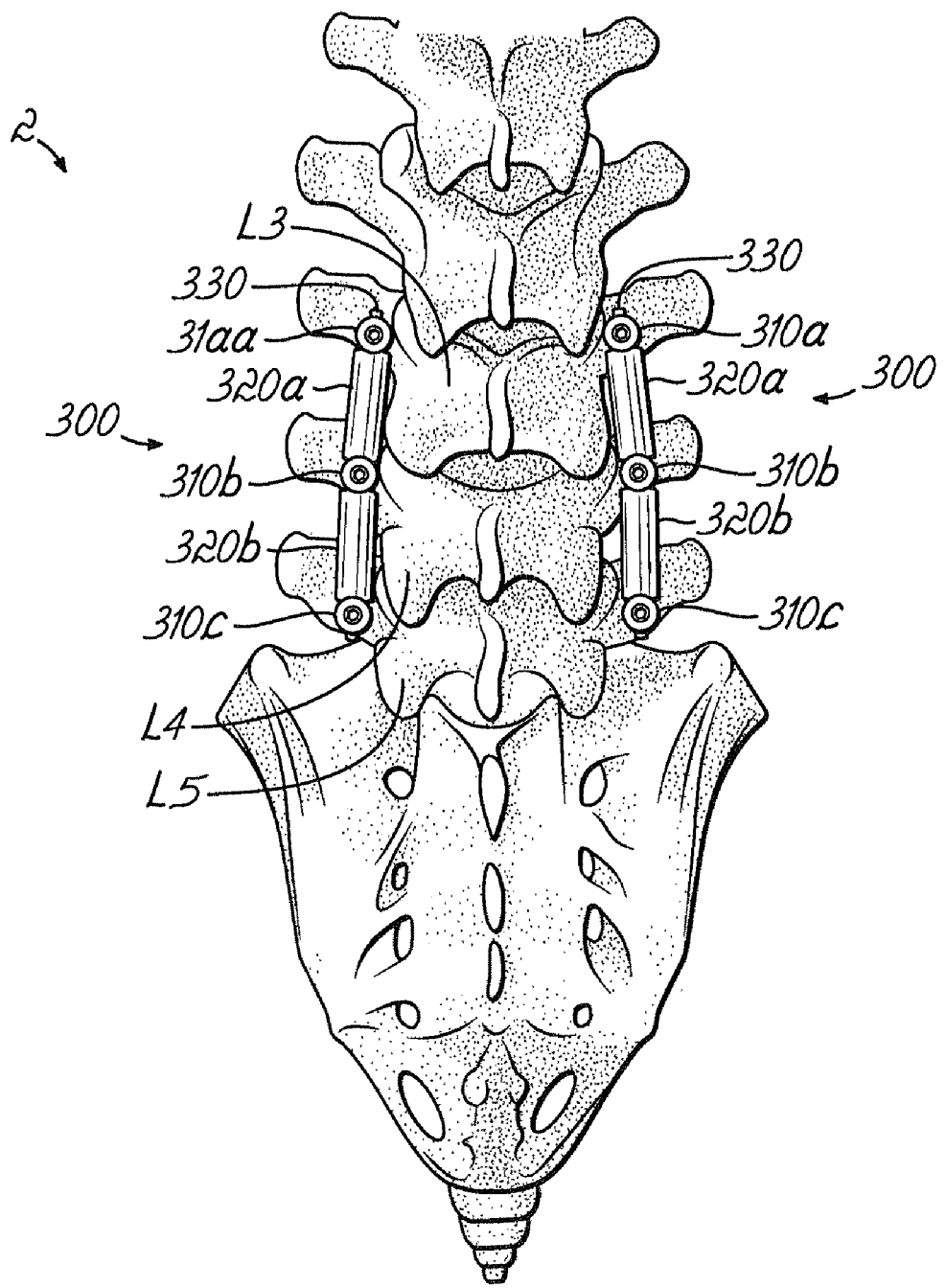
FIG. 6 is a posterior elevation view of a human spinal column with two multi-level spinal stabilization devices according to an embodiment of the present invention implanted therein.

FIG. 6 depicts a posterior elevation view of a human spinal column with two multi-level spinal stabilization devices 300 according to an embodiment of the present invention implanted therein to stabilize the L3, L4 and L5 vertebrae. As shown in FIG. 6, each stabilization device 300 includes three bone anchors, in this case pedicle screws 310a, 310b and 310c, rigid spacers 320a and 320b, and a metal cord 330. In the illustrated embodiment, the pedicle screws 310a, 310b and 310c are implanted in the L3, L4, and L5 vertebrae, respectively. As will be apparent to those skilled in the art, the present invention also includes stabilization devices having more than two levels.

As illustrated, the spacer 320a is disposed between the pedicle screws 310a and 310b, and the spacer 320b is disposed between the pedicle screws 310b and 310c, and the cord 330 extends through the pedicle screws 310a, 310b, 310c and the spacers 320a and 320b. The pedicle screws 310a, 310b, 310c, the spacers 320a, 320b, and the cord 330 may be constructed and configured to operate substantially the same as the corresponding components described above with respect to the single level stabilization device 100.

In one embodiment of the multi-level stabilization device 300, the cord 330 may be clamped to each of the pedicle screws 310a, 310b and 310c. Alternatively, the cord 330 may be clamped only to the two distal-most pedicle screws 310a and 310c. In one embodiment, the cord 330 may be tensioned to different degrees for different levels. For example, the segment of the cord 330 between the pedicle screws 310a and 310b be may be highly tensioned, while the segment of the cord 330 between the pedicle screws 310b and 310c may be tensioned to a lesser amount. As a result, the stabilization system 300 will be more rigid between the pedicle screws 310a and 310b than between 310b and 310c. Accordingly, fixation of the L3 and L4 vertebrae will be more rigid than fixation of the L4 and L5 vertebrae. As discussed above, the use of a metal cable or wire for the cord 330 allows for a much wider range of stiffness of the portion between any pair of pedicle screws as compared to an existing dynamic stabilization system. Thus, in a multi-level system, a stabilization device with a more patient-specific, side-specific, and level-specific stiffness profile can be achieved.

Figure 7:
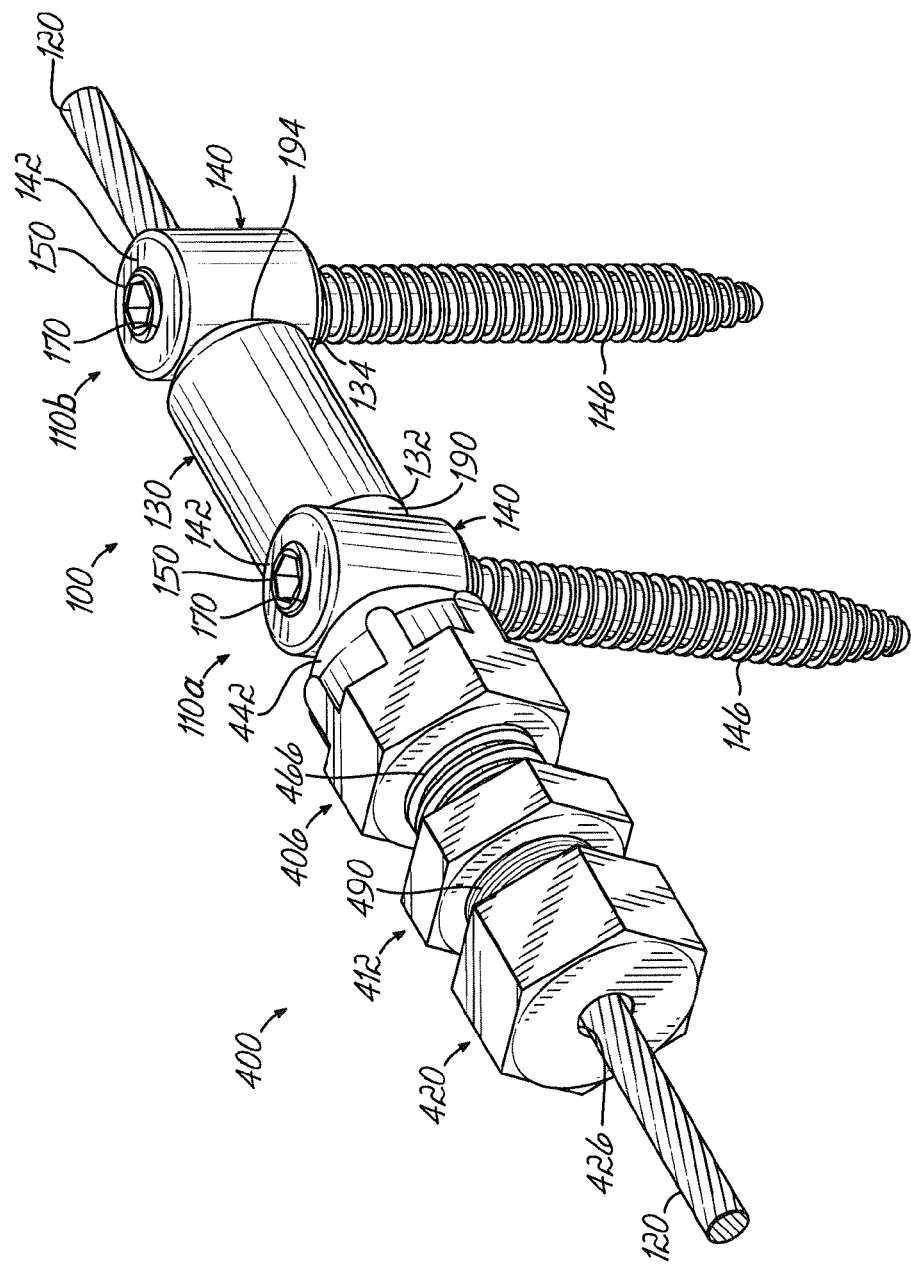
FIG. 7 is a perspective view of a stabilization device including an exemplary tensioning mechanism according to one embodiment of this invention.
Figure 8:
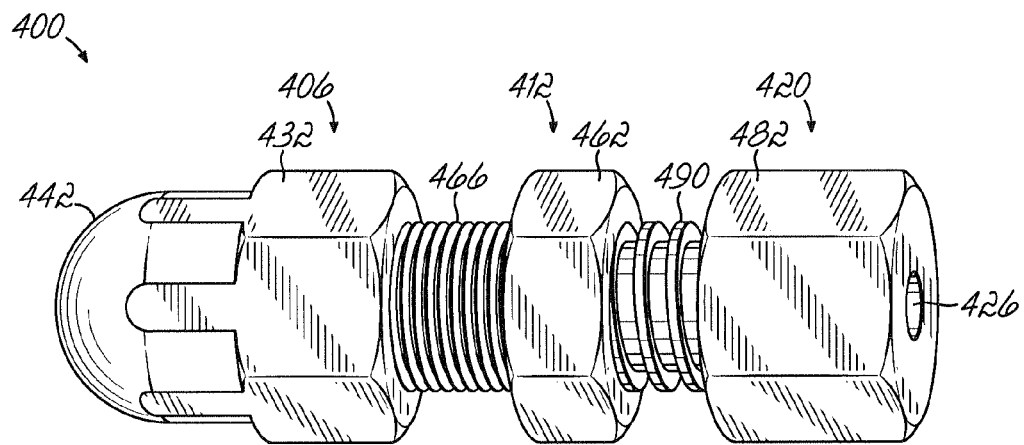
FIGS. 8-9 are views of the tensioning mechanism of FIG. 7.
Figure 9:
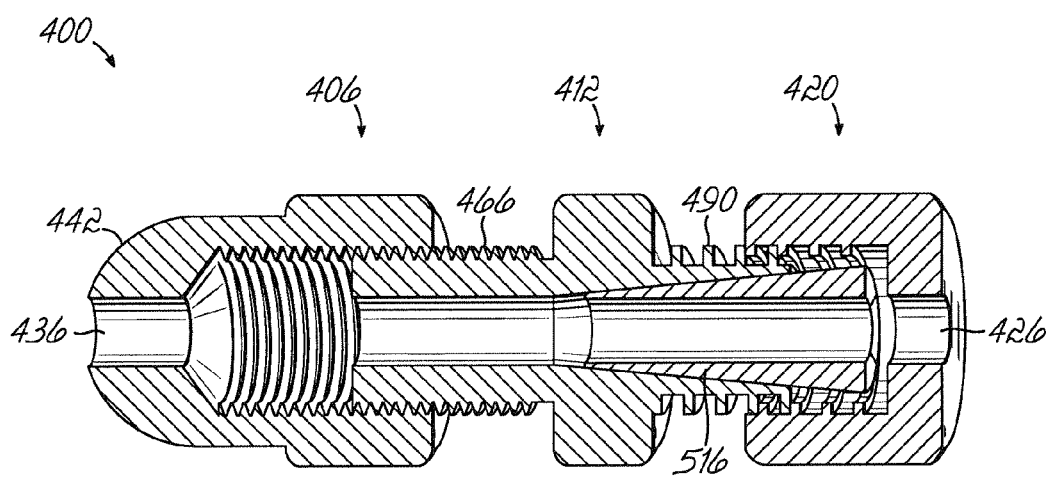

FIG. 7 is a perspective view of a stabilization device 100 including an exemplary tensioning mechanism 400 according to one embodiment of the present invention. The tensioning mechanism operates to permit the surgeon to apply the desired amount of tension to the cord 120. As shown in FIGS. 7-9, the tensioning mechanism 400 may include a cable tensioning nut 406, a body 412, a collet tightening nut 420, and a collet 516. (Tensioning mechanism 400 can be utilized for a cable 120 or cord 120 but is described in terms of a cable 120). The cable tensioning nut 40 may be that portion of the tensioning mechanism 400 that contacts the head portion 140 of the pedicle screw 110. The collet tightening nut 420 may be positioned on the opposite side of the body 412 from the cable tensioning nut 406. The collet 516 may be positioned around the cable 120 and in an interior portion of the body 412. One end of the collet 516 may be contacted by the collet tightening nut 420.

Each of the cable tensioning nut 402, body 412, and collet tightening nut 420 may further include flats 432, 462, and 482, respectively, which are configured to be engaged by a tool, such as a wrench, for holding or turning that portion of the cable tensioning device 400. Other tool engaging structures may likewise be incorporated in other designs. The collet tightening nut 420 may further include a cable exit hole 426 and the cable tensioning nut 406 may further include a cable entrance hole 436 and a pedicle screw contact surface 442. The body 412 may further include external threads 466 that cooperate with internal threads on the cable tensioning nut 406 and external threads 490 that are engaged with internal threads on the collet tightening nut 420. The body 412 may further include a shaped interior hollow portion (also known as a bore, cavity or passage) in a shape that tapers downwardly from the collet tightening nut 420 towards the cable tensioning unit 406.

In operation, the cable tensioning device 400 is first slipped over the wire 120 until the pedicle screw contact surface 442 of the cable tensioning nut 406 contacts the head 140 of the pedicle screw 110. The body 412 is then grasped by a wrench or other tool such that it can be prevented from twisting or moving around the cable 120. The collet tightening nut 420 may then be grasped and rotated such that the collet 516 is pushed through the internal channel in the body 412 towards the cable tensioning unit 406. Because of the tapering hollow portion in the body 412 the collet will be pressed, tightened or crimped inwards around the cable 120. The collet tightening nut 420 may push the collet 516 into the hollow portion of the body 412 far enough to effectively secure the collet 516, and therefore the body 412, to the cable 120 in that position. It has been found that once the collet tightening nut 420 is tightened and the collet 516 is secured around the cable 516, loosening the collet tightening nut 420 does not then allow the body 412 or the cable tensioning device 400 as a whole to slide over the cable 120 again. In alternative embodiments, however, such a releasable system may be realized.

The body 412 may then be again secured (or may still be secured from before) and the cable tensioning nut 406 may be rotated such that threads on the cable tensioning nut 406 interact with the external threads 466 of the body 412 so as to push the body 412, collet 516, and collet tightening nut 420 away from the head 140 of the pedicle screw 110. This action, in effect, lengthens the cable tensioning device such that, because the body 412 and cable tensioning nut 406 are secured in relation to one section of the cable 120 by action of the collet 516, the cable 120 is drawn through the head 140 of the pedicle screw 110. The body 412 is moved by continued rotation of the cable tensioning nut 406 until the desired tension on cable 120 is achieved. The set screw 150 is then tightened in the head 140 of the pedicle screw 110 to secure the cable 120 in the desired position.

After the set screw 150 is tightened so as to secure the cable 120, the cable tensioning nut 406 is then rotated in the opposite direction so as to provide some amount of slack in the cable 120 between the cable tensioning device 400 and the head 140 of the pedicle screw 110. The cable 120 can then be cut between the cable tensioning device 400 and the head 140 so as to trim and remove the excess cable and the cable tensioning device 400.

As may be appreciated, in further embodiments various cord tensioning devices may be employed, such as, for example, the use of pliers or other devices to pull the cord to the desired tension.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

I claim:

1. An implantable orthopedic system for stabilizing first, second and third vertebrae of a spinal column, the system comprising:
   a cord;
   a first bone anchor configured to be secured to the first vertebra, a second bone anchor configured to be secured to the second vertebra, and a third bone anchor configured to be secured to the third vertebra, wherein each bone anchor comprises:
   a bone attachment portion, and
   a head portion attached to the bone attachment portion, the head portion including a channel sized to receive the cord therethrough, wherein the channel extends through the head portion from a first end surface to a second end surface opposite the first end surface of the head portion, and a clamping mechanism adapted to secure the cord to the bone anchor; and
   first and second spacers each having a channel sized to receive the cord therethrough, wherein the channel extends from a first end surface of the spacer to a second end surface of the spacer,
   wherein the first spacer is positionable between the head portion of the first bone anchor and the head portion of the second bone anchor and to maintain a predetermined spacing between the first bone anchor and the second bone anchor,
   wherein the second spacer is positionable between the head portion of the second bone anchor and the head portion of the third bone anchor to maintain a predetermined spacing between the second bone anchor and the third bone anchor,
   wherein a first portion of the cord extending through the channel of the first spacer and secured between the first bone anchor and the second bone anchor is tensioned a first amount while a second portion of the cord extending through the channel of the second spacer and secured between the second bone anchor and the third bone anchor is tensioned a second amount, the second amount of tension being less than the first amount of tension such that fixation between the first and second vertebrae is more rigid than fixation between the second and third vertebrae.

2. The system of claim 1, further comprising:
   a cord tensioning device having a first end and a second end wherein the first end is adjacent to the second end surface of the head portion of the first bone anchor, wherein the second end surface of the head portion of the first bone anchor has a geometry, wherein the first end of the cord tensioning device has a geometry that complements the geometry of the second end surface of the head portion of the first bone anchor so as to be multi-directionally pivotable relative to the second end surface of the head portion of the first bone anchor.

3. The system of claim 2, wherein the geometry of the second end surface of the head portion of the first bone anchor is concave and the geometry of the first end of the cord tensioning device is convex.

4. An implantable orthopedic system for stabilizing first, second and third vertebrae of a spinal column, the system comprising:
   a cord;
   a first bone anchor configured to be secured to the first vertebra, a second bone anchor configured to be secured to the second vertebra, and a third bone anchor configured to be secured to the third vertebra, wherein each bone anchor comprises:
   a bone attachment portion, and
   a head portion attached to the bone attachment portion, the head portion including a first concave face and a second concave face oriented about 180 degrees from the first concave face, a cord receiving portion extending through the head portion from the first concave face to the second concave face, and a clamping mechanism adapted to secure the cord to the bone anchor; and first and second spacers each having a channel sized to receive the cord therethrough, wherein the first spacer is adapted to be positioned between the head portions of the first and second bone anchors and to maintain a predetermined spacing between the same, and the second spacer is adapted to be positioned between the head portions of the second and third bone anchors and to maintain a predetermined spacing between the same;

wherein each spacer further comprises a first end surface disposed on a first end, a second end surface disposed on a second end and a peripheral surface extending between the first end surface and the second end surface, the first and second end surfaces configured so as to be multi-directionally pivotable relative to the head portions of the bone anchors;

wherein the first end surface of the first spacer is substantially convex and configured to engage the first concave face of the head portion of the first bone anchor, and the second end surface of the first spacer is substantially convex and configured to engage the first concave face of the head portion of the second bone anchor;

wherein the first end surface of the second spacer is substantially convex and configured to engage the second concave face of the head portion of the second bone anchor, and the second end surface of the second spacer is substantially convex and configured to engage the first concave face of the head portion of the third bone anchor;

wherein a first portion of the cord extending through the channel of the first spacer and secured between the first bone anchor and the second bone anchor is tensioned a first amount while a second portion of the cord extending through the channel of the second spacer and secured between the second bone anchor and the third bone anchor is tensioned a second amount, the second amount being less than the first amount.

5. The system of claim 4 wherein the clamping mechanism includes a set screw and the head portion of each of the first, second and third bone anchors includes a screw aperture and a threaded hole for receiving the set screw.

6. The system of claim 4 further comprising a cord tensioning device.

7. The system of claim 6 wherein the cord tensioning device further comprises:
a body with a first end and a second end;
a collet disposed in the interior passage of the body, the interior passage tapered from the second end of the body towards the first end of the body;
a cord tensioning nut rotatably attached to the first end of the body; and
a collet tightening nut rotatably attached to the second end of the body.

8. The system of claim 7 wherein each of the body, collet, cord tensioning nut and collet tightening nut include a bore therethrough for receiving the cord.

9. The system of claim 4 wherein the diameter of the channel of each spacer is larger in at least one end of the spacer than at a middle portion of the spacer.

10. The system of claim 4 wherein in an assembled and implanted state each of the bone anchors is implanted into a respective vertebra, the first spacer is positioned between the first and second bone anchors and adjacent the head portions with the channel generally aligned with the cord receiving portions, the second spacer is positioned between the second and third bone anchors and adjacent the head portions with the channel generally aligned with the cord receiving portions, and wherein the cord extends through the cord receiving portions and the channels and is secured to the bone anchors by the respective clamping mechanisms.

11. The system of claim 4 wherein the peripheral surface of each of the spacers is generally cylindrical in shape.

12. The system of claim 4 wherein each spacer is made from one or more of stainless steel, titanium, stainless steel alloys and titanium alloys.

13. The system of claim 4 wherein each spacer is made from a polymer.

14. The system of claim 4, wherein the first amount of tension permits pivotable movement between the first spacer and the first and second bone anchors, and the second amount of tension prevents pivotable movement between the second spacer and the second and third bone anchors.

15. A method of stabilizing a portion of a spinal column of a patient comprising:
implanting first, second and third bone anchors into respective first, second and third vertebrae, wherein each bone anchor includes a head portion including a cord receiving portion extending through the head portion from a first spherically concave end face to a second spherically concave end face;
placing a first spacer between the head portions of the first and second bone anchors such that a first spherically convex end surface of the first spacer is engaged with the first spherically concave end face of the first bone anchor and a second spherically convex end surface of the first spacer is engaged with the first spherically concave end face of the second bone anchor, wherein the first spacer includes a channel adapted to receive a cord therethrough;
placing a second spacer between the head portions of the second and third bone anchors such that a first spherically convex end surface of the second spacer is engaged with the second spherically concave end face of the second bone anchor and a second spherically convex end surface of the second spacer is engaged with the first spherically concave end face of the third bone anchor, wherein the second spacer includes a channel adapted to receive a cord therethrough;
passing a cord through the cord receiving portions of the head portions of the first, second and third bone anchors and the channels of the first and second spacers; applying a first amount of tension to a first portion of the cord extending between the first and second bone anchors with the cable tensioning device such that the head portions of the first and second bone anchors exert a desired compressive force on the first spacer;
applying a second amount of tension to a second portion of the cord extending between the second and third bone anchors while maintaining the first amount of tension in the first portion of the cord such that the head portions of the second and third bone anchors exert a desired compressive force on the second spacer, the second amount of tension being different from the first amount of tension.

16. The method of claim 15 wherein the first amount of tension permits pivotable movement between the first spacer and the first and second bone anchors.

17. The method of claim 16 wherein the second amount of tension prevents pivotable movement between the second spacer and the second and third bone anchors.

18. The method of claim 15 further comprising removing the excess cord after applying the second amount of tension.

19. The method of claim 15, wherein the second amount of tension is less than the first amount of tension such that fixation between the first and second vertebrae is more rigid than fixation between the second and third vertebrae.

20. The method of claim 15, wherein the first amount of tension is less than the second amount of tension such that fixation between the second and third vertebrae is more rigid than fixation between the first and second vertebrae.

21. A method of stabilizing a portion of a spinal column of a patient comprising:
  implanting first, second and third bone anchors into first, second and third vertebrae, respectively, wherein each bone anchor includes a head portion including a channel sized to receive a cord therethrough, wherein the channel extends through the head portion from a first end face to a second end face;
  placing a first spacer between the head portions of the first and second bone anchors wherein the first spacer includes a channel adapted to receive a cord therethrough;
  placing a second spacer between the head portions of the second and third bone anchors, wherein the second spacer includes a channel adapted to receive a cord therethrough;
  passing a cord through the cord receiving portions of the first, second and third bone anchors and the channels of the first and second spacers such that a first portion of the cord extends through the channel of the first spacer between the head portions of the first and second bone anchors and a second portion of the cord extends through the channel of the second spacer between the head portions of the second and third bone anchors;
  applying a tensile load to the cord such that the head portions of the bone anchors trimming the excess cord applying a first amount of tension to the first portion of the cord and a second amount of tension to the second portion of the cord, the second amount of tension being less than the first amount of tension; and
  securing the cord to the first, second and third bone anchors such that the first portion of the cord maintains the first amount of tension between the head portions of the first and second bone anchors and the second portion of the cord maintains the second amount of tension between the head portions of the second and third bone anchors such that fixation between the first and second vertebrae is more rigid than fixation between the second and third vertebrae.

* * * * *

UNITED STATES PATENT AND TRADEMARK OFFICE
CERTIFICATE OF CORRECTION

| | | |
|---|---|---|
| PATENT NO. | : 7,842,072 B2 | Page 1 of 1 |
| APPLICATION NO. | : 11/377476 | |
| DATED | : November 30, 2010 | |
| INVENTOR(S) | : John Dawson | |

It is certified that error appears in the above-identified patent and that said Letters Patent is hereby corrected as shown below:

Column 12
Lines 9-10, delete "applying a tensile load to the cord such that the head portions of the bone anchors trimming the excess cord".

Signed and Sealed this
Fourteenth Day of June, 2011

David J. Kappos
*Director of the United States Patent and Trademark Office*